(12) United States Patent
Madaus et al.

(10) Patent No.: US 9,808,590 B2
(45) Date of Patent: Nov. 7, 2017

(54) METHOD AND DEVICE FOR CARRYING OUT A SIGNAL-PROCESSING VIEWING OF A MEASUREMENT SIGNAL THAT IS CORRELATED TO THE RESPIRATORY ACTIVITY OF AN INDIVIDUAL

(71) Applicant: ResMed R&D Germany GmbH, Martinsried (DE)

(72) Inventors: Stefan Rolf Madaus, Graefelfing (DE); Jorg Meier, Martinsried (DE); Dieter Heidmann, Geretsried (DE); Hartmut Schneider, Lutherville, MD (US)

(73) Assignee: RESMED R&D GERMANY GMBH, Martinsried (DE)

( * ) Notice: Subject to any disclaimer, the term of this patent is extended or adjusted under 35 U.S.C. 154(b) by 77 days.

(21) Appl. No.: 14/248,771

(22) Filed: Apr. 9, 2014

(65) Prior Publication Data

US 2014/0290656 A1    Oct. 2, 2014

Related U.S. Application Data

(63) Continuation of application No. 12/662,323, filed on Apr. 12, 2010, now Pat. No. 8,728,000, which is a
(Continued)

(30) Foreign Application Priority Data

Oct. 17, 2002    (DE) .................................. 102 48 590

(51) Int. Cl.
*A61B 5/08*    (2006.01)
*A61M 16/00*    (2006.01)
(Continued)

(52) U.S. Cl.
CPC ......... *A61M 16/0069* (2014.02); *A61B 5/085* (2013.01); *A61B 5/087* (2013.01);
(Continued)

(58) Field of Classification Search
CPC .............. A61M 16/00; A61M 16/0069; A61M 2230/005; A61M 2230/40; A61M 2205/52; A61B 5/4818; A61B 5/08
See application file for complete search history.

(56) References Cited

U.S. PATENT DOCUMENTS 3,996,928 A * 12/1976 Marx ................. A61B 5/02055
                                                       600/484
4,777,962 A    10/1988 Watson et al.
(Continued)

FOREIGN PATENT DOCUMENTS

JP    2000-504602    4/2000
JP    2002-505924    2/2002
(Continued)

OTHER PUBLICATIONS

Translation of Japanese Official Action issued for Japanese Patent Application No. 2004-544264.
(Continued)

*Primary Examiner* — Patricia Mallari
*Assistant Examiner* — Karen Toth
(74) *Attorney, Agent, or Firm* — Nixon & Vanderhye P.C.

(57) ABSTRACT

The invention relates to a method and device for carrying out a signal-processing viewing of a measurement signal that is correlated with the respiratory activity of an individual, for example, of a measurement signal that is correlated with the respiratory gas. The aim of the invention is to provide solutions with which an improved electronic analysis of the signals that are representative with regard to respiratory activity can be achieved. To this end, the invention provides that viewing results are obtained within the scope of a signal-processing viewing of said measurement signal and make a differentiation between obstructive and central respiratory disorders possible. The viewing results are determined, in particular, while taking into account changes of
(Continued)

Figure 1:
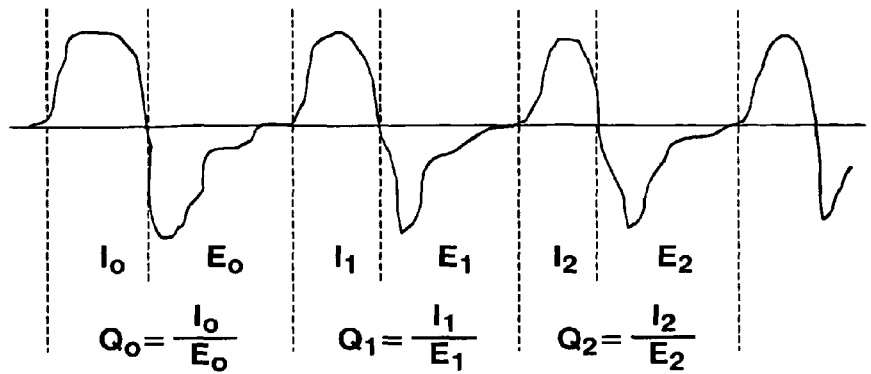

Consideration of the inspiration/expiration ratio selected breathing characteristics such as, for example, the change in the ratio of inhalation time to exhalation time.

19 Claims, 2 Drawing Sheets

Related U.S. Application Data continuation of application No. 10/531,476, filed as application No. PCT/EP03/11524 on Oct. 17, 2003, now Pat. No. 7,722,546.

(51) Int. Cl.
*A61B 5/087* (2006.01)
*A61F 5/56* (2006.01)
*A61B 5/085* (2006.01)
*A61B 5/00* (2006.01)

(52) U.S. Cl.
CPC .......... *A61B 5/4836* (2013.01); *A61B 5/7239* (2013.01); *A61B 5/7282* (2013.01); *A61F 5/56* (2013.01); *A61M 16/00* (2013.01); *A61M 16/0003* (2014.02); *A61M 16/0051* (2013.01); *A61B 5/7275* (2013.01); *A61M 2016/0018* (2013.01); *A61M 2016/0033* (2013.01); *A61M 2016/0036* (2013.01); *A61M 2230/005* (2013.01)

(56) References Cited

U.S. PATENT DOCUMENTS

| | | | |
|---|---|---|---|
| 4,972,842 A | 11/1990 | Korten et al. | |
| 5,146,918 A | 9/1992 | Kallok et al. | |
| 5,259,373 A * | 11/1993 | Gruenke ............... | A61M 16/00 128/204.18 |
| 5,335,654 A * | 8/1994 | Rapoport ................. | 128/204.23 |
| 5,385,144 A | 1/1995 | Yamanishi et al. | |
| 5,704,345 A | 1/1998 | Berthon-Jones | |
| 5,803,066 A | 9/1998 | Norman et al. | |
| 5,964,720 A * | 10/1999 | Pelz ..................... | A61B 5/0002 600/483 |
| 6,015,388 A | 1/2000 | Sackner et al. | |
| 6,029,665 A | 2/2000 | Berthon-Jones | |
| 6,085,747 A | 7/2000 | Axe et al. | |
| 6,105,575 A | 8/2000 | Mechlenburg et al. | |
| 6,165,133 A | 12/2000 | Rapoport et al. | |
| 6,261,238 B1 | 7/2001 | Gavriely | |
| 6,287,264 B1 | 9/2001 | Hoffman | |
| 6,363,933 B1 | 4/2002 | Berthon-Jones | |
| 6,530,372 B1 * | 3/2003 | Madaus et al. .......... | 128/204.23 |
| 6,651,652 B1 | 11/2003 | Wård | |
| 6,739,335 B1 | 5/2004 | Rapport et al. | |
| 6,752,151 B2 | 6/2004 | Hill | |
| 6,814,074 B1 | 11/2004 | Nadjafizadeh et al. | |
| 7,438,686 B2 | 10/2008 | Cho et al. | |
| 7,722,546 B2 | 5/2010 | Madaus et al. | |
| 8,348,941 B2 | 1/2013 | Tehrani | |
| 2002/0043264 A1 | 4/2002 | Wickham | |
| 2002/0183642 A1 * | 12/2002 | Murphy ................. | A61B 5/061 600/532 |
| 2003/0045806 A1 | 3/2003 | Brydon | |
| 2003/0078619 A1 * | 4/2003 | Bonnet et al. .................... | 607/4 |
| 2003/0158466 A1 * | 8/2003 | Lynn ........................ | A61B 5/00 600/300 |
| 2004/0230105 A1 | 11/2004 | Geva et al. | |
| 2006/0037615 A1 | 2/2006 | Wilkinson et al. | |
| 2007/0149860 A1 | 6/2007 | Lynn et al. | |
| 2007/0150022 A1 | 6/2007 | Ujhazy et al. | |
| 2011/0263997 A1 * | 10/2011 | Corn ............................ | 600/529 |

FOREIGN PATENT DOCUMENTS

| | | |
|---|---|---|
| WO | WO 97/28838 | 8/1997 |
| WO | WO 99/45989 | 9/1999 |
| WO | 02 47747 A | 6/2002 |
| WO | 03 059158 A | 7/2003 |

OTHER PUBLICATIONS

Office Action issued in corresponding German Application No. 102 48 590.9 issued on Sep. 9, 2011 and received on Oct. 5, 2011 (with translation).
Parent, U.S. Appl. No. 12/662,323, filed Apr. 12, 2010, Madaus et al.

* cited by examiner

Consideration of the inspiration/expiration ratio

Consideration of the variation in characteristic features of the curve shape of successive inspiration cycles Consideration of the changes in curve shape features for successive expiration cycles Interval 0   Interval 1   Interval 2   Interval 3

Consideration of the variation in curve shape features in an interval within successive inspiration cycles - Consideration of the variation in the lengths of defined intervals in successive inspiration cycles

METHOD AND DEVICE FOR CARRYING OUT A SIGNAL-PROCESSING VIEWING OF A MEASUREMENT SIGNAL THAT IS CORRELATED TO THE RESPIRATORY ACTIVITY OF AN INDIVIDUAL

This application is a continuation of U.S. application Ser. No. 12/662,323, filed Apr. 12, 2010, now allowed, which is a continuation of U.S. application Ser. No. 10/531,476, filed Apr. 15, 2005, now U.S. Pat. No. 7,722,546, which is the US national phase of international application PCT/EP2003/011524 filed Oct. 17, 2003, which designated the U.S. and claims priority of DE 102 48 590.9, filed Oct. 17, 2002, the entire contents of each of which are hereby incorporated by reference.

The invention concerns a method of and an apparatus for carrying out signal-processing consideration of a measurement signal related to respiration activity, for example the respiratory gas flow, in particular for matching pressure regulation in the administration of a breathable gas at a pressure level which at least in phase-wise manner is above the ambient pressure, and generally for the diagnosis and/or therapy of sleep-related breathing disorders.

To treat sleep-related breathing disorders it is known to supply a patient with a respiratory gas, in particular ambient air, at a pressure level which is above the ambient pressure level at least in phase-wise manner. The administration of the respiratory gas at an increased pressure level makes it possible to implement pneumatic splinting in the region of the upper respiratory tracts, whereby it is possible to preclude any obstructions in that respiratory tract region in a physiologically highly compatible fashion.

Particularly good compatibility of the supply of the respiratory gas at an elevated pressure level is achieved if the respiratory gas pressure is set to a pressure which is as low as possible and which is only sufficient for obstruction prevention or obstruction limitation. It is known to implement setting of the instantaneously required respiratory gas pressure, having regard to the evaluation results of signal-processing consideration of the instantaneous respiratory gas flow, by means of an electronic pressure regulating device which is integrated into a CPAP unit. The instantaneous respiratory gas flow can be detected in particular by volume flow sensors, for example measurement orifices.

In the case of CPAP units with automatic pressure matching the electronic pressure regulating device is configured with the aim that the respiratory gas pressure required is afforded with an adequate level of certainty, but on the other hand the dynamics of the variation in pressure are so slight that the sleep pattern of the patient is not noticeably adversely affected by the changes in the respiratory gas pressure. Adverse effects can occur in particular if comparatively high respiratory gas pressure levels are temporarily set.

The object of the present invention is to provide ways with which it is possible to achieve electronic evaluation, which is accurate with a high degree of probability, of a signal that is representative in respect of respiration activity, so that, based on that evaluation, the physiological state of a patient can be accurately determined and/or the respiratory gas supply, in particular the respiratory gas pressure, can be matched to the instantaneous physiological demands in an improved manner.

In accordance with the invention that object is attained in that, in the context of signal-processing consideration of a measurement signal which is indicative of the respiratory gas flow, consideration results are obtained which permit differentiation between obstructive and central breathing disorders.

In that way it is advantageously possible, in connection with detection of the instantaneous respiratory gas flow, to implement an analysis of trends, by virtue of which it is possible to carry out the measures which are most suitable for eliminating or preventing an instantaneous or impending breathing disorder, in particular involving matching the pressure regulating characteristics.

In accordance with a particularly preferred embodiment of the invention signal-processing consideration is effected in such a way that the inspiration time and the expiration time for successive breaths is detected thereby. By determining the ratio of the inspiration time and the expiration time and by considering the variation in respect of time of those ratios, it is possible to recognise a trend as to whether imminent breathing disorders or breathing disorders which already exist are caused obstructively and/or centrally.

In particular in combination with that measure, or also alternatively thereto, it is also possible to obtain information in respect of an existing or imminent disorder phase from comparative consideration of successively occurring changes in properties of the derivatives and in particular the first derivative of the respiratory gas flow in the region of the breathing phase change.

The ratio of inspiration time Ix to expiration time Ex can be used to describe breathing disorders. In particular a trend in the variation in the duration of the inspiration time with respect to the expiration time can give an indication of an imminent obstruction in the upper respiratory tracts. Furthermore, consideration of the ratio of inspiration time Ix to expiration time Ex in a trend analysis procedure can contribute to distinguishing obstructive from central apneas.

Exact measurement of the respiratory gas flow 'flow curve' is particularly advantageous.

The ratio of inspiration to expiration can be referred to as the duty cycle and represents an information carrier for assessment of the respiratory flow disturbances in the upper respiratory tracts. If flow limitations actually occur, the inspiration time seemingly increases. The nasally measured resistance of the upper respiratory tracts in contrast remains unchanged. If it is assumed that the breathing minute volume remains constant, it is possible to deduce a relationship between the volume flow, the inspiration duration and the breath duration. (The breath minute volume is equal to the volume flow multiplied by the inspiration time and divided by the breath duration.)

In particular in combination with that measure or also alternatively thereto it is also possible to obtain information for an existing or imminent-disturbance phase from comparative consideration of successively occurring changes in properties of the derivatives of the—or within the—respiratory cycles, in particular the first derivative of the respiratory gas flow in the region of the breathing phase change.

Consideration of the differential can be directed to the beginning of the inspiration cycle and/or to the end of the inspiration cycle and also to consideration of the curve shape during the inspiration cycle.

The average gradient can be calculated in simple form for intervals which extend for example over 10% of the time duration of the respective breathing phase.

The gradient (for example the maximum gradient at the phase change) can also be calculated floatingly within a window over the inspiration cycle.

The trend analysis in particular in respect of the nature and constitution of the respiratory drive is preferably implemented having regard to/with the inclusion of the signal evaluation results set forth hereinafter:
- max. peak flow during the inspiration cycle
- the breath volume
- the inspiration time, and
- the second derivative of the measured flow curve.

In accordance with a further aspect of the invention signal-processing consideration is effected on the basis of consideration of the differential at the beginning of the expiration cycle or at the end of the expiration cycle respectively. The differential can be calculated in a simple form over an interval of for example 10% at the beginning of the expiration cycle and after the expiratory maximum flow or computed floatingly over the expiration cycle. Evaluation can advantageously be effected in a similar fashion to that described hereinbefore, with the inclusion of the maximum peak flow during the expiration cycle, the breath volume and/or the expiration time and/or the second derivative (curvature) of the measured flow curve during the expiration cycle. The evaluation procedure also makes it possible to afford information about the nature and the constitution of the upper respiratory tracts.

The flattening of the respiratory flow curve during the inspiration cycle can be interpreted in accordance with the model of the Starling resistor as a flow limitation. Consideration of the configuration of the curve shape during the inspiration cycle in an interval between for example 10% after the beginning of the inspiration cycle and 10% before the end thereof can advantageously provide information about the elastic properties of the upper respiratory tracts. It is also possible in that way to draw a conclusion about the Pcrit-value (the pressure at which the upper respiratory tracts close).

The signal processing procedure advantageously embraces in particular analysis of the number of local maxima and minima, the amplitude of the local maxima and minima, the sequence of the magnitude of the amplitudes of local maxima and minima and the frequency involved in the sequence of the local maxima and minima.

In accordance with a further aspect of the present invention the signal processing procedure according to the invention preferably also includes spectral consideration and consideration in respect of amplitude of a snoring signal and on the basis thereof can furnish information about the nature of the elastic properties of the upper respiratory tracts and possibly about the nature and location of the closure in the upper respiratory tracts.

In accordance with a particular aspect signal-processing evaluation and the trend analysis based thereon are effected on the basis of combined consideration of at least two parameters as specified hereinafter. Trend analysis is preferably based on consideration of the variation in the ratios of the parameters when considered in combination:
- inspiration time
- expiration time
- breath duration and breath frequency
- breath volume during the inspiration cycle
- breath volume during the expiration cycle
- first differential and second differential of the respiratory flow
- amplitudes of local maxima and local minima
- frequency of local maxima and local minima
- inflexion points
- maximum inspiratory flow and maximum expiratory flow.

Signal-processing consideration of the above-specified parameters can give information about the following:
- the nature of the upper respiratory tracts inter alia for distinguishing between central and obstructive apneas
- the elastic properties of the upper respiratory tracts (restoring modulus, modulus of elasticity)
- the location of an obstruction
- the degree of severity of a sleep apnea
- the Pcrit-value.

Figure 2:
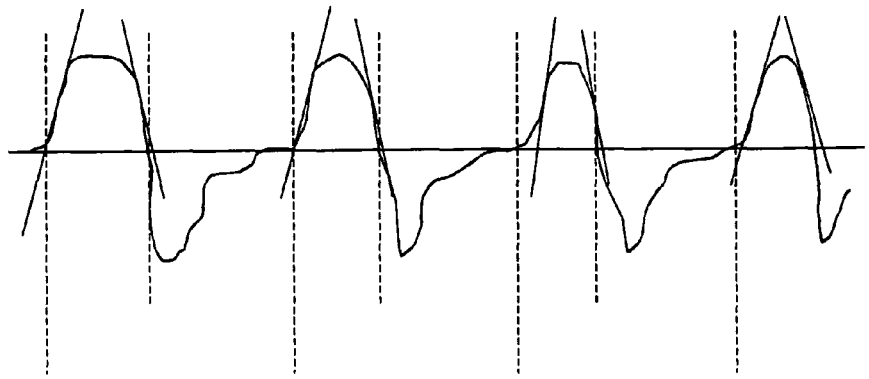
Figure 3:
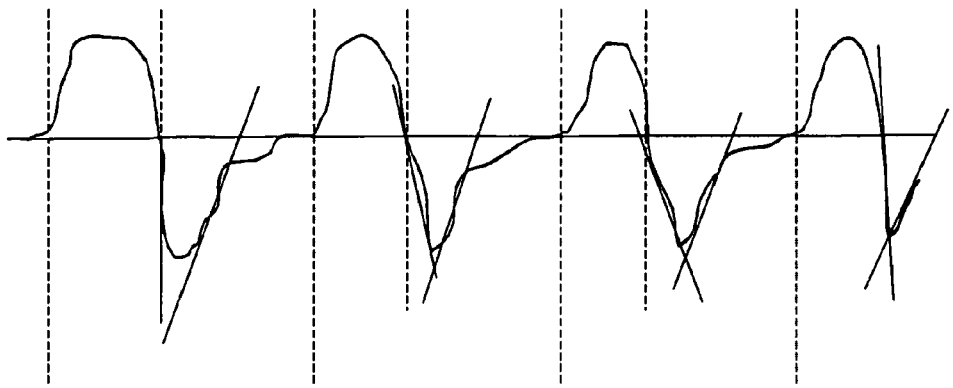
Figure 4:
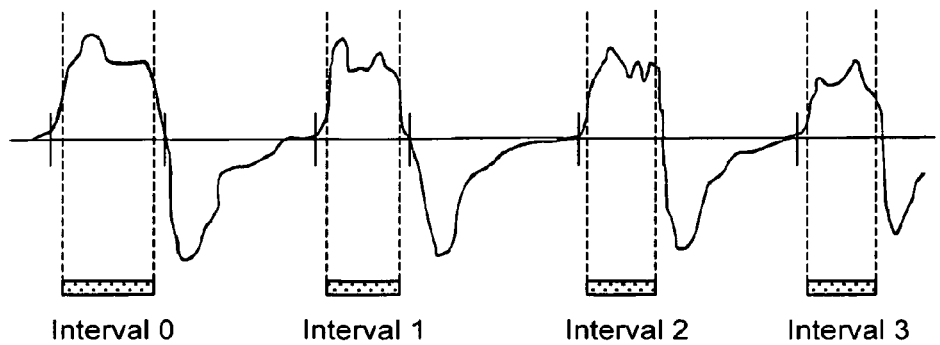

Further details and features will be apparent from the description hereinafter with reference to the drawing in which:

FIG. 1 shows a part of a respiratory gas flow chart to explain signal-processing consideration on the basis of ascertaining the ratios of the inspiration duration to the expiration duration for successive respiratory cycles, FIG. 2 shows a part of a respiratory gas flow chart to explain signal-processing consideration on the basis of consideration of the change in the curve shape features of successive inspiration cycles, FIG. 3 shows a part of a respiratory gas flow chart to explain signal-processing consideration on the basis of consideration of the change in the curve shape features of successive expiration cycles, and FIG. 4 shows a part of a respiratory gas flow chart to explain signal-processing consideration on the basis of evaluation of curve shape features within intervals in successive inspiration cycles.

FIG. 1 shows a part from a respiratory gas flow chart for explaining signal-processing consideration on the basis of ascertaining the ratios of the inspiration duration to the expiration duration for successive respiratory cycles.

The ratio of inspiration time Ix to expiration time Ex and in particular the variation thereof for successive respiratory cycles represents information which is indicative in respect of the occurrence of breathing disorders. In particular a trend in the change in the duration of the inspiration time with respect to the expiration time can give a pointer to imminent obstruction in the upper respiratory tracts. In addition consideration of the ratio of inspiration time Ix to expiration time Ex in a trend analysis can contribute to differentiating obstructive from central apneas. Measurement of the respiratory gas flow, which is as accurate as possible, and therewith possible depiction of the flow curve is advantageous.

The ratio of inspiration to expiration can be referred to as the duty cycle and represents an information carrier for assessment of the respiratory flow disturbances in the upper respiratory tracts. If flow limitations actually occur, the inspiration time seemingly increases. The nasally measured resistance of the upper respiratory tracts in contrast remains unchanged.

If it is assumed that the breathing minute volume remains constant, it is possible to deduce a relationship between the volume flow, the inspiration duration and the breath duration. (The breath minute volume is equal to the volume flow multiplied by the inspiration time and divided by the breath duration.)

FIG. 2 shows a part of a respiratory gas flow chart to explain signal-processing consideration on the basis of consideration of the change in curve shape features of successive inspiration cycles. The chart in FIG. 2 illustrates the mean gradient ascertained by way of the first derivative of the respiratory gas flow at the beginning of the inspiration cycle and at the end of the inspiration cycle respectively. That mean gradient is calculated in a simple form over for example a 10% interval or calculated floatingly over the inspiration cycle. Further curve shape features that can be taken into consideration are in particular the extreme values of the respiratory gas flow (peak flow during the inspiration cycle) and/or the breath volume and/or the inspiration time and/or the second derivative of the detected flow curve. Evaluation of those curve shape features—and in particular consideration of the variation thereof—permits information to be obtained about the nature and the constitution of the breathing drive, that is to say the instantaneous physiological state of the patient or the physiological state which prevails shortly.

FIG. 3 shows a part from a respiratory gas flow chart for explaining signal-processing consideration on the basis of consideration of the change in curve shape features of successive expiration cycles, in particular in the form of evaluation of the differential at the beginning of the expiration cycle or at the end of the expiration cycle respectively as can be ascertained in a simple form for example for a 10% interval at the beginning of the expiration cycle and after the expiratory maximum flow or floatingly over the expiration cycle.

Similarly as specified for FIG. 2, in this case also further curve shape features which can be taken into consideration are in particular the extreme values of the respiratory gas flow (peak flow during the expiration cycle) and/or the breath volume and/or the expiration time and/or the second derivative of the detected flow curve. Evaluation of those curve shape features—and in particular consideration of the variation thereof—permits information to be obtained about the nature and the constitution of the breathing drive, that is to say the instantaneous physiological state of the patient or the physiological state which prevails shortly.

FIG. 4 shows a part of a respiratory gas flow chart to explain a signal-processing consideration procedure on the basis of evaluation of curve shape features with intervals in successive inspiration cycles.

The flattening of the respiratory flow curve during the inspiration cycle can be interpreted (in accordance with the model of the Starling resistor) as a flow limitation. Consideration of the pattern of the curve shape during the inspiration cycle in an interval between for example 10% after the beginning of the inspiration cycle and 10% before the end thereof gives information for example about the elastic properties of the upper respiratory tracts.

This analysis also makes it possible to draw conclusions about the Pcrit-value (pressure at which the upper respiratory tracts close).

In carrying out a trend analysis procedure in particular the following evaluation intermediate results are advantageously taken into consideration:
number of local maxima and minima
the amplitude of the local maxima and minima
the sequence of the magnitude of the amplitudes of local maxima and minima,
the frequency in the succession of the local maxima and minima
curve shape in an interval during the inspiration cycle
length of the intervals.

Spectral consideration and consideration in respect of amplitude of a snoring signal can further provide information about the nature of the elastic properties of the upper respiratory tracts and about the location and nature of the closure in the upper respiratory tracts.

The invention is not limited to the examples of use described hereinbefore. It can be employed in particular in controlling respiratory gas pressure and matching pressure regulation in a CPAP-unit by using a suitably configured signal processing device. It can also be employed in regard to time-displaced evaluation of a series of measurement data and in that situation permits visualisation of obstructively or centrally caused phases of disturbed respiration. The invention can also be used in conjunction with a pneumotachograph generally for investigating the sleep breathing of a patient without in that respect any disturbances of obstructive nature having to be simultaneously eliminated directly by a respiratory gas supply at increased pressure.

The invention claimed is:

1. A method of controlling pressure provided to a patient by a pressure regulating device, the method comprising:
providing a supply of respiratory gas at a first pressure level above ambient pressure level;
measuring a signal indicative of respiratory activity;
determining, using a signal processing device, an inspiration phase and an expiration phase of each breath from the signal;
detecting, using the signal processing device, an inspiration time and an expiration time of each breath for successive breaths;
determining, using the signal processing device, a ratio of the inspiration time to the expiration time for each said breath;
detecting, using the signal processing device, a variation in the ratio;
determining, using the signal processing device, presence of obstruction of the upper respiratory tract based on the in the ratio;
and adjusting the first pressure level based on the determined presence of obstruction.

2. The method according to claim 1, wherein the first pressure level is increased based on the determined presence of obstruction of the upper respiratory tract.

3. The method according to claim 1, wherein the presence of obstruction of the upper respiratory tract is determined based on comparative analysis of successively occurring changes in the ratio of the inspiration time to the expiration time.

4. The method according to claim 1, wherein the signal indicative of respiratory activity is a flow signal.

5. The method of claim 4, further comprising determining a first derivative of flow from the flow signal.

6. The method of claim 5, wherein the first derivative of flow is determined for a region of phase change in each breath.

7. The method of claim 6, wherein the determining of the presence of obstruction of the upper respiratory tract includes determining changes in the first derivative of flow over successively occurring breaths.

8. The method according to claim 6, wherein the region of phase change is directed to at least one of the beginning of the inspiration phase and the end of the inspiration phase.

9. The method of claim 5, further comprising analyzing a curve shape during the inspiration phase.

10. The method of claim 9, further comprising calculating an average gradient in simple form for intervals that extend over a predetermined percentage of a time duration of the inspiration phase.

11. The method of claim 10, further comprising variably calculating a gradient at a phase change within a window over the inspiration phase.

12. The method according to claim 10, wherein the predetermined percentage is at least 50%.

13. The method according to claim 10, wherein the predetermined percentage is 80%.

14. The method according to claim 13 wherein the curve shape during the inspiration phase is analysed in an interval between 10% after the beginning of the inspiration phase and 10% before the end of the inspiration phase.

15. The method according to claim 9, wherein the analysis of the curve shape includes determining a number of local maxima and minima, an amplitude of the local maxima and minima, a sequence of the magnitude of amplitudes of the local maxima and minima, and a frequency of the sequence of the local maxima and minima.

16. The method according to claim 9, further comprising determining a Pcrit value and using the Pcrit value in adjusting the first pressure level.

17. An apparatus configured to carry out the method set forth in claim 1.

18. The method according to claim 1, wherein the variation of inspiration time is a relative increase in inspiration time.

19. The method according to claim 1, wherein the variation of inspiration time corresponds to a flattening of a respiratory flow curve during the inspiration phase.

* * * * *

UNITED STATES PATENT AND TRADEMARK OFFICE
CERTIFICATE OF CORRECTION

PATENT NO. : 9,808,590 B2
APPLICATION NO. : 14/248771
DATED : November 7, 2017
INVENTOR(S) : Madaus et al.

Page 1 of 1

It is certified that error appears in the above-identified patent and that said Letters Patent is hereby corrected as shown below:

In the Claims

Claim 1 Column 6, Line 28, change "the in the ratio;" to --the variation in the ratio;--.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*